United States Patent [19]

Mason et al.

[11] Patent Number: 5,012,019

[45] Date of Patent: Apr. 30, 1991

[54] PROCESS FOR PURIFYING AROMATIC NITRATION PRODUCTS

[75] Inventors: Robert W. Mason, Lake Charles; Peter C. Imm, Sulphur; Paul J. Craney, Lake Charles; Thomas W. Offill, Lake Charles; Robert T. Brooker, Lake Charles, all of La.

[73] Assignee: Olin Corporation, Cheshire, Conn.

[21] Appl. No.: 449,259

[22] Filed: Jan. 26, 1990

[51] Int. Cl.$^5$ ............................................. C07C 205/11
[52] U.S. Cl. ............................................. 568/934; 568/932; 568/939; 568/940; 252/194; 423/395; 423/397
[58] Field of Search ............... 252/194; 423/395, 397; 568/934, 940, 932, 939

[56] References Cited

U.S. PATENT DOCUMENTS

| | | | |
|---|---|---|---|
| 1,798,175 | 3/1931 | Smith | 252/194 |
| 1,844,862 | 2/1932 | Mohler | 423/395 |
| 2,017,980 | 10/1935 | McQuaid | 423/395 |
| 3,885,926 | 5/1975 | Manning et al. | 252/194 X |
| 3,957,889 | 5/1976 | Milligan et al. | 568/937 |
| 3,981,975 | 9/1976 | Coon | 423/390 |
| 4,371,721 | 2/1983 | Wu | 568/939 |
| 4,410,746 | 10/1983 | Eckler | 568/943 |
| 4,438,083 | 3/1984 | Willems et al. | 423/395 |
| 4,724,132 | 2/1988 | Fabry | 423/395 |
| 4,918,250 | 4/1990 | Mason et al. | 568/934 |

*Primary Examiner*—Robert L. Stoll
*Assistant Examiner*—Chhaya Sayala
*Attorney, Agent, or Firm*—Dale Lynn Carlson

[57] ABSTRACT

The present invention relates to a process for purifying an aromatic nitration product mixture comprising a nitrated aromatic compound, water, and nitric or sulfuric acid which comprises without regard to sequence: (a) removing at least a portion of said water from said product mixture by contacting and reacting said water in said mixture with magnesium nitrate trihydrate to form magnesium nitrate pentahydrate or magnesium nitrate hexahydrate and removing said magnesium nitrate pentahydrate or magnesium nitrate hexahydrate from said nitrated aromatic compound in said product mixture, and (b) removing at least a portion of said acid from said product mixture by contacting and reacting said acid with an ionic or non-ionic absorbent to form a reacted absorbent and removing said reacted absorbent from said nitrated aromatic compound in said product mixture.

3 Claims, No Drawings

PROCESS FOR PURIFYING AROMATIC NITRATION PRODUCTS

This invention relates generally to a process for purifying aromatic nitration reaction products.

Nitration reactions of aromatic hydrocarbons are generally conducted in mixed acid systems, such as mixed nitric and sulfuric acids. However, these mixed acid systems usually involve reconcentration of the spent sulfuric acid after the nitration reaction since the sulfuric acid acts as a dessicant for the by-product water formed during the nitration reaction. The by-product water is then removed from the sulfuric acid using a high temperature flash procedure. This reconcentration step is time consuming, energy intensive and requires the use of expensive materials of construction.

If the nitration reaction is conducted in concentrated nitric acid in the absence of sulfuric acid, distillaton of the nitric acid phase from the reaction effluent is necessary in order to effect water removal from the nitric acid and regeneration of the concentrated nitric acid. Unfortunately, the energy requirement for this operation is as great as the energy required to reconcentrate sulfuric acid in the mixed acid system.

New methods for removing by-product water from aromatic nitration product mixtures that are less energy intensive would be highly desired by the aromatic nitration community.

In one aspect, the present invention relates to a method for removing water from an aromatic nitration product mixture which comprises reacting at least a portion of said water in said product mixture with magnesium nitrate trihydrate to form magnesium nitrate pentahydrate or magnesium nitrate hexahydrate, and removing the magnesium nitrate pentahydrate or magnesium nitrate hexahydrate from the product mixture.

In another aspect, the present invention relates to a continuous process for separating water from an aqueous aromatic nitration product mixture which comprises the steps of:

(a) contacting said water in said aqueous aromatic nitration product mixture with magnesium nitrate trihydrate for a time sufficient to form magnesium nitrate pentahydrate or magnesium nitrate hexahydrate, (b) removing the magnesium nitrate pentahydrate or magnesium nitrate hexahydrate from the product mixture, (c) heating said magnesium nitrate pentahydrate or magnesium nitrate hexahydrate to an elevated temperature sufficient to form magnesium nitrate trihydrate and water, and (d) repeating steps (a) through (c) in a continuous fashion including adding the magnesium nitrate trihydrate formed in step (c) to satisfy at least a portion of the step (a) requirement for magnesium nitrate trihydrate.

In yet another aspect, the present invention relates to a process for purifying an aromatic nitration product mixture comprising a nitrated aromatic compound, water, and nitric or sulfuric acid which comprises without regard to sequence:

(a) removing at least a portion of said water from said product mixture by contacting and reacting said water in said mixture with magnesium nitrate trihydrate to form magnesium nitrate pentahydrate or magnesium nitrate hexahydrate and removing said magnesium nitrate pentahydrate or magnesium nitrate hexahydrate from said nitrated aromatic compound in said product mixture, and (b) removing at least a portion of said acid from said product mixture by contacting and reacting said acid with an ionic or non-ionic absorbent to form a reacted absorbent and removing said reacted absorbent from said nitrated aromatic compound in said product mixture These and other aspects will become apparent upon reading the following detailed description of the invention.

The present invention provides an excellent alternative to the conventional high energy needs associated with heating large acid streams in order to distill the water therefrom. In contrast, it has now been found in accordance with the present invention that the water can be recovered in a more energy efficient manner by utilizing magnesium nitrate trihydrate as a dessicant for the water. Solid magnesium nitrate trihydrate is preferably added to the nitration product mixture, and recovery of the pentahydrate or hexahydrate salt is suitably effected by recrystallization of the salt. In order to recover the trihydrate salt, the magnesium nitrate pentahydrate or magnesium nitrate hexahydrate is then suitably heated, preferably to a temperature of between about 120° C. and about 140° C., to regenerate magnesium nitrate trihydrate.

The absorbent useful in the process of the present invention is suitably any ionic or non-ionic absorbent that selectively reacts with the acid or inorganic salt that is desired to be removed from the nitration product mixture. Illustrative of such absorbents are weakly basic ion exchange resins such as AMBERLITE IRA-93, an anionic polystyrene polamine resin, a product of Rohm & Haas Corporation. The preferable range for the product mixture to be contacted with the absorbent when using a dinitrotoluene (DNT) product mixture on a weight percent basis is between about 75% and about 90% DNT, between about 10% and about 25% of aqueous (50%-70%) nitric acid, between about 0% and about 10% of magnesium nitrate hexahydrate, and between about 0% and about 5% of aqueous (98%) sulfuric acid.

The present invention is expected to be useful in the purification of aromatic nitration product mixtures, such as, for example, product mixtures that are obtained from the nitration of aromatic compounds such as benzene and toluene. Particularly advantageous results are envisioned in minimizing energy costs in the production of dinitrotoluene (DNT). The present invention is suitably utilized, without limitation, in mixed acid (nitric plus sulfuric acid) systems, as well as systems employing nitric acid as the sole acid. The invention is suitably utilized in conjunction with single step nitration reactions, as well as multistep nitration reactions. Typically these nitration reactions are conducted at a temperature of between about 40° C. and about 80° C., preferably at a temperature of between about 50° C. and about 70° C.

The following examples are intended to illustrate, but in no way limit the scope of, the present invention.

PROPOSED EXAMPLE 1

CONCENTRATION OF NITRIC ACID USING MAGNESIUMNITRATE TRIHYDRATE

A warm solution of 69.7 grams of magnesium nitrate trihydrate and 50.6 grams of 70% aqueous nitric acid is cooled stepwise and filtered at each temperature Point.

Solid magnesium nitrate hexahydrate is recovered in the following amounts: 35.31 grams at 35° C., 12.05 grams at 20° C., and 6.18 grams at 0° C. The recovered 98% nitric acid filtrate (16.42 grams) is suitable for use in aromatic nitration reactions.

PROPOSED EXAMPLE 2

USE OF MAGNESIUM NITRATE TRIHYDRATE TO REMOVE WATER FROM A NITRATED AROMATIC PRODUCT MIXTURE

A warm, 70° C. mixture of 146 grams of 61% HN03, 33 grams of 98% H2S04, 124 grams of magnesium nitrate trihydrate and 50 grams of dinitrotoluene (DNT) is allowed to phase separate to 56 grams of acidic dinitrotoluene and 295 grams of inorganic acid solution. Toluene extraction of the aqueous layer removed 6.2 grams of DNT, and the toluene-DNT mixture is recycled to the nitration reactor. After chilling to 0° C., 150 grams of magnesium nitrate hexahydrate is separated from 135 grams of a concentrated nitric/sulfuric acid mixture. The recovered acid is suitable for recycle to the nitration reactor.

PROPOSED EXAMPLE 3

PURIFICATION OF A NITRATED AROMATIC PRODUCT MIXTURE USING AN ION EXCHANGE RESIN

Toluene is reacted to dinitrotoluene in 98% nitric acid and magnesium nitrate trihydrate. After excess nitric acid removal by distillation and organic-aqueous acid phase separation, an organic phase is produced consisting of a mixture of 180 grams of dinitrotoluene, 20 grams of 60% nitric acid and 15 grams of magnesium nitrate hexahydrate. This mixture is passed through an electrically heated bed of 4000 grams of AMBERLITE XAD-2 ion exchange resin. The dinitrotoluene effluent is virtually free of inorganic impurities.

PROPOSED EXAMPLE 4

PRODUCT PURIFICATION IN A TWO-STEP NITRATION REACTION

Toluene is converted to dinitrotoluene in a two-step nitration sequence, first in a mixture of 70% nitric acid and magnesium nitrate hexahydrate, and then by dinitration in 98% nitric acid. After removal of excess anhydrous nitric acid by distillation, the dinitrotoluene - 75% nitric acid product mixture is combined with the aqueous nitric acid/magnesium nitrate phase from the mononitration step and phase separated. The resulting dinitrotoluene- aqueous nitric acid - magnesium nitrate organic layer is treated as in Example 3, but using AMBERLITE IRA-93 ion exchange resin to produce a clean, salt-free dinitrotoluene product.

What is claimed is:

1. A method for removing water from an aromatic nitration product mixture which comprises reacting at least a portion of said water in said product mixture with magnesium nitrate trihydrate to form magnesium nitrate pentahydrate or magnesium nitrate hexahydrate, and removing the magnesium nitrate pentahydrate or magnesium nitrate hexahydrate from the product mixture.

2. A continuous process for separating water from an aqueous aromatic nitration product mixture which comprises the steps of:
    (a) contacting said water in said aqueous aromatic nitration product mixture with magnesium nitrate trihydrate for a time sufficient to form magnesium nitrate pentahydrate or magnesium nitrate hexahydrate,
    (b) removing the magnesium nitrate pentahydrate or magnesium nitrate hexahydrate from the product mixture,
    (c) heating said magnesium nitrate pentahydrate or magnesium nitrate hexahydrate to an elevated temperature sufficient to form magnesium nitrate trihydrate and water, and
    (d) repeating steps (a) through (c) in a continuous fashion including adding the magnesium nitrate trihydrate formed in step (c) to satisfy at least a portion of the step (a) requirement for magnesium nitrate trihydrate.

3. A process for purifying an aromatic nitration product mixture comprising a nitrated aromatic compound, water, and nitric or sulfuric acid which comprises without regard to sequence:
    (a) removing at least a portion of said water from said product mixture by contacting and reacting said water in said mixture with magnesium nitrate trihydrate to form magnesium nitrate pentahydrate or magnesium nitrate hexahydrate and removing said magnesium nitrate pentahydrate or magnesium nitrate hexahydrate from said nitrated aromatic compound in said product mixture, and
    (b) removing at least a portion of said acid from said product mixture by contacting and reacting said acid with an ionic or non-ionic absorbent to form a reacted absorbent and removing said reacted absorbent from said nitrated aromatic compound in said product mixture.

* * * * *